(12) United States Patent
Das et al.

(10) Patent No.: US 7,763,436 B2
(45) Date of Patent: Jul. 27, 2010

(54) METHOD FOR THE DIAGNOSIS OF RHEUMATOID ARTHRITIS

(75) Inventors: Hasi Rani Das, Delhi (IN); Bhawna Gupta, Delhi (IN); Sunil Kumar Raghav, Ghaziabad (IN); Kalyan Goswami, Wardha (IN); Charu Agrawal, Delhi (IN); Rakha Hari Das, Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 12/271,149

(22) Filed: Nov. 14, 2008

(65) Prior Publication Data

US 2009/0130690 A1     May 21, 2009

Related U.S. Application Data

(63) Continuation of application No. 11/281,243, filed on Nov. 16, 2005, now abandoned.

(30) Foreign Application Priority Data

Nov. 11, 2004    (IN)    ................. 2272/DEL/2004

(51) Int. Cl.
*G01N 33/53*     (2006.01)
(52) U.S. Cl. ........................ 435/7.1; 436/518
(58) Field of Classification Search ........................ None
See application file for complete search history.

(56) References Cited

U.S. PATENT DOCUMENTS

| 4,208,479 | A | * | 6/1980 | Zuk et al. ..................... 435/7.9 |
| 6,130,049 | A | | 10/2000 | Paul et al. |
| 6,638,723 | B1 | | 10/2003 | Kim |
| 6,858,438 | B2 | | 2/2005 | Van Venrooij et al. |
| 6,890,720 | B1 | | 5/2005 | Serre et al. |

OTHER PUBLICATIONS

Co-pending U.S. Appl. No. 11/281,243 entitled "Novel Diagnostic Marker, A Diagnostic Kit And A Method For Diagnosis Of Rheumatoid Arthritis", to Hasi Rani Das filed Nov. 16, 2005; available in PAIR.
Office Action issued on Jul. 11, 2007 for U.S. Appl. No. 11/281,243.
Office Action issued on Sep. 24, 2007 for U.S. Appl. No. 11/281,243.
Final Office Action issued on Nov. 24, 2008 for U.S. Appl. No. 11/281,243.
Seelen et al. Clin. Exp. Immunology 2003 vol. 134, p. 335-343.
Takahashi et al. Clin. Exp. Immunology 2004 vol. 136, p. 585-590.
Steiner et al., Z. Rheumatol., 2002, 61(6): 667-73, Abstract.
Sibilia, Presse Med., 2000, 29(31), 1723-30, Abstract.
Holmskov et al., Immunol. Today, 1994, 15:67-74, Abstract.
Malhotra et al., 1995, Nat Med. 237-243, Abstract.

* cited by examiner

*Primary Examiner*—Jacob Cheu
(74) *Attorney, Agent, or Firm*—Meyertons, Hood, Kivlin, Kowert & Goetzel, P.C.; Eric B. Meyertons

(57) ABSTRACT

The present invention relates to a novel diagnostic marker useful for the diagnosis of rheumatoid arthritis comprising the autoantibodies of mannose binding lectin protein and a process thereof.

4 Claims, 3 Drawing Sheets

METHOD FOR THE DIAGNOSIS OF RHEUMATOID ARTHRITIS

PRIORITY CLAIM

This application is a continuation application of U.S. patent application Ser. No. 11/281,243 entitled "A NOVEL DIAGNOSTIC MARKER, A DIAGNOSTIC KIT AND A METHOD FOR DIAGNOSIS OF RHEUMATOID ARTHRITIS", filed on Nov. 16, 2005 which claims priority to Indian Patent Application No. 2272/DEL/2004 entitled: "A NOVEL DIAGNOSTIC MARKER, A DIAGNOSTIC KIT AND A METHOD FOR DIAGNOSIS OF RHEUMATOID ARTHRITIS" filed on Nov. 11, 2004.

FIELD OF INVENTION

The present invention relates to a novel diagnostic marker useful for the diagnosis of rheumatoid arthritis. Further, it relates to a method for the diagnosis of rheumatoid arthritis in the human subject. More particularly, it relates to measure the autoantibodies to Mannose binding lectin (MBL) from human serum and quantifying the level of the autoantibodies to the mannose binding lectin (MBL) protein. The present invention also relates to a diagnostic kit for diagnosis of Rheumatoid arthritis.

BACKGROUND OF INVENTION

Rheumatoid arthritis (RA) is a chronic systemic inflammatory disease with peripheral synovitis as its main manifestation. The presentation of the disease and the progression is highly variable both within and between the individuals. The disease is thought to occur as an immunological response to an as yet unidentified antigen. The prevalence of RA is 1 to 2 percent of the general population and is found worldwide. Females with RA outnumber males by a 3:1 margin. The symptoms and the signs of the disease may vary from joint complaints like pain, stiffness and functional impairment, to more constitutional complaints like fatigue and detrimental to general health. The current paradigm for rheumatoid arthritis suggests that persistent synovitis leads to erosive joint damage, progression of which results in functional disability. Because of this variety in disease expression a huge number of outcome variables have been used in the past decades to evaluate interventions in clinical trials.

Diagnostic and prognostic markers are relevant tools in the management of many medical conditions because they help to identify and stratify patients into different risk groups, enabling treatment to be targeted appropriately in order to reduce morbidity and mortality. An evidence-based approach to identify the most valuable diagnostic markers for a given disease is clearly important. Biological markers will play an important role in the development and the early monitoring of disease modifying anti-rheumatic drugs with respect to future radiographic progression.

The diagnosis of rheumatoid arthritis has been hampered by the lack of a truly disease-specific serologic marker and thus diagnosis of RA is mainly based on clinical criteria recommended by the American College of Rheumatology. Studies have shown that 40-83% of subsequent progression of rheumatoid arthritis can be predicted by a combination of prognostic factors such as joint involvement, high levels of C-reactive protein and RF positivity. There are similar findings for predictors of functional disability in studies. Till date the most consistent diagnostic feature has been RF positivity, which is equally important in predicting joint damage and functional disability. Immunoglobulin A RF and the co-presence of RF with anti-keratin or anti-filaggrin antibodies may increase levels of prediction. Other potentially useful antibodies include anti-RA33 autoantibodies and antibodies to the stress protein BiP, which seem to have higher specificity than RF for predicting RA outcome. Apart from being promising diagnostic markers these autoantibodies or the underlying cellular autoimmune reactions, respectively, may also play a role in the pathogenesis of RA (Steiner G, Smolen J S. Z Rheumatol. 2002 December; 61 (6): 667-73). Added value of genetic predictors over that of RF remains inconclusive.

To date, only the rheumatoid factor and anti-filaggrin antibodies (including anti-stratum corneum or "anti-keratin" and anti-perinuclear factors) have been used with sufficiently acceptable standards for diagnostic purpose. IgM rheumatoid factors can be detected in about 80% of patients with rheumatoid arthritis but they lack specificity since they are also found in other autoimmune conditions (lupus, Sjogren's syndrome), in chronic infections, and in certain lymphoproliferative syndromes (with or without cryoglobulinemia). Anti-filaggrin antibodies are more specific (70 to 100% depending on the study) but can only be detected in 30 to 50% of the patients. High titers of rheumatoid factor (IgM and/or IgA) and anti-filaggrin antibodies are factors of poor prognosis because they are associated with destructive polyarthritis, sometimes complicated with extra-articular signs (nodules, vasculitis). Antigens derived from filaggrin have been used for their diagnostic purposes in rheumatoid polyarthritis (U.S. Pat. No. 6,890,720). Among the new autoantibodies being studied, only anti-Sa appears to have real diagnostic and prognostic value but the recent data must be confirmed (Sibilia J, Presse Med. 2000 Oct. 21; 29 (31): 1723-30).

Moreover, first described as a marker for RA in 1964, anti-perinuclear factor (APF) was directed to constituents of the keratohyaline granules later found to contain the protein filaggrin. Despite its specificity for RA, because of exacting technical requirements, APF never became widely used. Anti-keratin antibodies (AKA), first described in 1979, bound filaggrin bound keratin in senescent esophageal cells. As was APF, AKA had greater specificity for RA than RF. Anti-perinuclear factor (APF) and anti keratin antibodies (AKA), two tests known for a long time, have a high specificity of up to 70% for RA. The tests are done by immunofluorescence but did not become popular in clinical practice, despite high specificity, due to various technical difficulties in performing the assays. Filaggrin was identified as the antigen that was targeted by both these autoantibodies. Antibodies to Sa antigen have also been detected in sera of patients with RA but its association with RA has not been confirmed. Besides Peptides immunoreactive with autoantibodies from patients with rheumatoid arthritis (U.S. Pat. No. 6,858,438), autoantibodies from a body fluid that react with a microtubule organizing center (MTOC) (U.S. Pat. No. 6,638,723), measurement of depressed activity of catalytic antibodies (U.S. Pat. No. 6,130,049) have also been suggested as diagnostics of rheumatoid arthritis.

Mannose binding lectin (MBL) is an acute phase serum protein that has a significant role in innate immunity. This C type lectin with specific binding affinity to mannose and N-acetyl glucosamine (GlcNAc) is structurally homologous to C1q, the component to classical complement pathway (Holmskov et al, Immunol Today 1994; 15: 67-74). On binding to the specific carbohydrate, its associated serine proteases (MBL associated serine proteases or MASP) get activated leading to activation of complement cascade; popularly described as lectin pathway. Consequently it has significant role in eliciting the inflammatory response and thus it has been well associated with the pathogenesis of RA. Particularly in RA, agalactosylated IgG (IgG0) that has an exposed GlcNAc can be an easy target for MBL binding leading to generation of inflammatory response (Malhotra et al, Nat Med 1995; 1: 237-243).

Recently in Systemic lupus erythematosus (SLE), a related autoimmune disorder, autoantibodies against MBL have been reported (Seelen M A et al, Clin Exp Immunol 2003; 134: 335-343, Takahashi R et al Clin Exp Immunol 2004; 136: 585-590). These anti-MBL autoantibodies in the sera of SLE patients have been shown to decrease the functional activity of MBL. The presence of anti-MBL autoantibodies in the sera of RA patients was determined for the first time in the present invention and thus represents a genuine discovery of a diagnostic and prognostic marker for RA. Our research makes it possible to demonstrate for the first time the presence of autoantibodies directed against MBL in serum of subjects suffering from RA.

OBJECTS OF INVENTION

The main object of the present invention is to provide a novel diagnostic marker useful for the diagnosis of rheumatoid arthritis.

Another object of the present invention is to provide a method for the diagnosis of rheumatoid arthritis in the human subject.

Further another object of the present invention is to provide a method to measure the autoantibodies to Mannose binding lectin (MBL) from human serum and quantifying the level of the autoantibodies to the mannose binding lectin (MBL) protein.

Still another object of the present invention is to provide a method to detect the level of disease activity and degree of joint damage (including the tenderness of the joints and the number of swollen joints) in the RA patient.

Yet another object of the present invention is to provide a diagnostic kit for diagnosis of Rheumatoid arthritis.

SUMMARY OF THE INVENTION

The present invention deals with a novel specific diagnostic marker for rheumatoid arthritis in the RA patients by identifying the presence of anti-MBL autoantibodies in serum sample obtained from the patient. The present invention particularly relates to anti-MBL autoantibodies as a highly sensitive diagnostic marker for identifying rheumatoid arthritis patients who possess specifically defined clinical disease-progression criteria. The present invention is also beneficial to detect the level of disease activity and degree of joint damage (including the tenderness of the joints and the number of swollen joints) in the RA patient. It also provides a sensitive and specific diagnostic marker than the commonly used rheumatoid factor (RF).

DETAILED DESCRIPTION OF THE INVENTION

Figure 1:
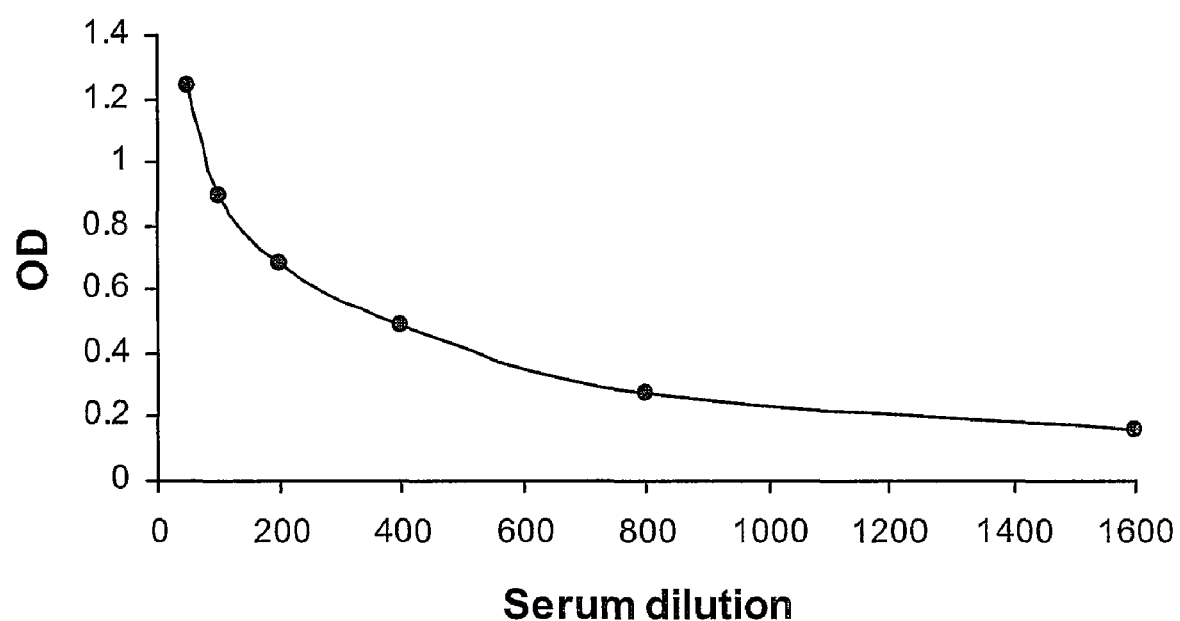
FIG. 1 represents the titration curve for anti-MBL antibodies using serial dilution of the standard serum. The serum sample of a patient with a higher value of the anti-MBL autoantibodies was taken as the standard and the autoantibody level measured at the optical density at 450 nm was considered as 1000 AU/mL.

Accordingly, the present invention provides a novel diagnostic marker useful for the diagnosis of rheumatoid arthritis comprising the autoantibodies of mannose binding lectin (MBL) protein.

In an embodiment of the present invention, the presence of said marker indicates the possibility of rheumatoid arthritis.

In another invention of the present invention, the specific level of said marker relates with the level of disease activity and the level of joint damage.

Further, the present invention provides a method for the diagnosis of rheumatoid arthritis in the human subject, wherein the said method comprising the steps of:
 a Screening of normal control individuals and rheumatoid arthritis patients for the diagnostic marker by quantifying the level of autoantibodies to MBL by ELISA in the blood of a human subject.
 b Statistically comparing the levels of autoantibodies to MBL in the Rheumatoid arthritis (RA) patients with that of the normal healthy individuals obtained from step (a) to establish association of rheumatoid arthritis disease with the elevated MBL autoantibodies.
 c Estimating the isotypes of rheumatoid factors (IgM RF and IgG RF) by the ELISA test followed by computing their association with rheumatoid arthritis disease.
 d Comparing the values of autoantibodies to MBL and the RF isotypes (IgM RF and IgG RF) obtained from step (c) for the diagnosis of RA, wherein the presence of anti MBL autoantibodies indicates the possibility of the rheumatoid arthritis.

In an embodiment of the present invention, the blood of normal control individuals is collected from Guru Teg Bahadur Hospital, Delhi, India.

In another embodiment of the present invention, the blood of RA patients is collected from Army Hospital, Department of Rheumatology, New Delhi, India.

In further another embodiment of the present invention, the level of MBL autoantibodies in a RA affected patient is significantly higher than a normal healthy individual.

In yet another embodiment of the present invention, the levels of MBL auto antibodies in RA patients is in the range from 311 to 1192 AU/mL.

In still another embodiment of the present invention, the level of MBL autoantibodies in the healthy controls is in the range from 177 to 752 AU/mL.

In still another embodiment of the present invention, the presence of significantly high levels of autoantibodies to MBL (P value<0.0001), is associated with high disease (RA) activity and joint damage in the RA patient as compared to healthy individuals with out any symptom of RA.

In still another embodiment of the present invention, the computational analysis for the comparison of the autoantibodies to MBL and RF isotypes (IgM RF and IgG RF) are carried out by known statistical tools.

In still another embodiment of the present invention, the computational analysis is carried out using world wide web available tests such Mann Whitney U Test, sensitivity and specificity under Bayesian model, positive predictive value (PPV), negative predictive value (NPV), positive likelihood ratio (PLR) and negative likelihood ratio (NLR), Receiver operating characteristic (ROC) and the like.

Further, the present invention also provides a diagnostic kit for diagnosis of Rheumatoid arthritis comprising:
 a purified or recombinant Mannose binding protein;
 b anti-MBL auto antibody serum standard;
 c requisite reconstitutable coating, washing and dilution buffers;
 d microtiter plates;

e secondary enzyme conjugated antibodies;
f Appropriate substrate reagent, stop solution.

The diagnosis of rheumatoid arthritis has been hampered by lack of a truly disease-specific serologic marker and thus a major problem in the timely identification and treatment of the disease. Although there are known substances for predicting RA and its progressions but they lack specificity and sensitivity, therefore there is a demand for other diagnostic markers. Thus anti-MBL autoantibodies found for the first time in RA and its detection at the early stage of the disease enhances their usefulness as a promising diagnostic and prognostic marker for rheumatoid arthritis. This invention thus specifically relates to a novel diagnostic marker for rheumatoid arthritis enabling its association with detection and progression of RA.

Present invention is to provide a highly sensitive diagnostic marker for identifying rheumatoid arthritis patients with specifically defined clinical disease-progression criteria. Still another object of the present invention is to provide a method for estimating the amount of anti-MBL autoantibodies in the sera of RA patients. This is the first time demonstration of significant presence of anti-MBL autoantibodies in the sera of RA patients and their association with RA in the early stage of the disease for the first time. In the present invention and thus represents a promising specific diagnostic marker for RA. This is also first time demonstration of association of the anti-MBL autoantibodies with clinical signs of disease severity at the time of patient inclusion and their potential usefulness as markers for prognosis. The benefit of the anti-MBL autoantibodies is also as a marker for disease activity and for joint damage (tenderness of joints and swelling of joints). The present invention is also helpful for predicting the disease outcome in the patients where the established marker like RF is not detected. The present invention relates to a method of diagnosis of an autoimmune disease rheumatoid arthritis (RA) in a human subject. It provides a hitherto unavailable diagnostic marker for susceptibility of this potentially life-threatening disease. In particular, the claimed invention is directed to measure the levels of autoantibodies to MBL in serum sample of human subject. The autoantibodies to MBL are diagnostic of RA in a subject having clinical symptoms or indicate genetic predisposition for developing RA in a subject who does not present RA symptoms.

Mannose-binding lectin (MBL) is a serum collectin that plays an important role in innate immunity. It is the only collectin that activates complement via its own pathway when its multiple heads bind to carbohydrates on the surface of the invading microorganisms (Fraser I P et al. 1998). There is a quaternary structure similarity between MBL and the complement protein C1q. Binding of MBL to a surface activates MBL associated serine proteases (MASPs), which are homologous to the C1q-associated proteases-C1r and C1s. The complement system is a major mediator of innate immune defense and contributes to many innate immune functions including inflammation, opsonization and lysis.

It is also known that MBL can recognize carbohydrate structures on antibodies, including the common IgG glycosylation variant, agalactosylated IgG0. It is demonstrated that MBL can induce complement activation by interacting with IgG0, which accumulates in the joint fluid of RA patients, leading to chronic inflammation (Malhotra R et al. 1995).

Serum MBL level is known to be strongly associated with the presence of variant MBL alleles (Madsen H O et al. 1998, Wallis R et al. 1999). The MBL gene (7.4 kb) located on the long arm of chromosome 10 at 10q11.2-q21 contains four exons. Differential distribution of the normal allele A and the three allelic variants (D, B and C) due to mutation in the codons 52, 54 and 57 respectively on exon 1 and those present within the promoter region at position −550 and −221 are reported in various populations (Liscombe R J et al. 1992, Madsen H O et al. 1998, Wallis R et al. 1999). In the Indian population, we did not find any association of these gene variants with RA.

Human sera may be sampled and collected for the purpose of practicing the methods of the present invention. Collecting a serum sample encompasses the means of in vivo sampling directly from a subject, for example, by blood draw. Serum samples may be stored before analysis by well known storage means that will preserve a sample in an analyzable condition, such as quick freezing. The autoantibodies to MBL are diagnostic of RA in a subject having clinical symptoms or indicate genetic predisposition for developing RA in a subject who does not present RA symptoms.

For purposes of the present invention "measurement of serum levels of autoantibodies to MBL" from a serum sample of a subject to "quantify their level" encompasses the conventional means of amassing sufficient serum for analysis. A method for the present invention, for detecting in a human subject a susceptibility to RA, serum purified MBL was used as the antigen to coat the flat microtiter ELISA plates.

The present invention provides a rapid and accurate diagnostic test for diagnosing RA. It can be applied diagnostically in conjunction with other diagnostic tests in suspected cases of RA to confirm a diagnosis of RA. Previously available diagnostic tests for RA are limited in their diagnostic effectiveness. Therefore, the methods for the present invention provide a useful diagnostic test for RA that significantly enhances the existing diagnostic armamentarium for RA.

In addition, it is contemplated that the diagnostic test of the present invention can be used therapeutically to detect and treat RA patients with specific levels of autoantibodies to MBL.

The methods of the present invention is superior to previously available diagnostic tools for RA, because the present invention can be applied so that a person not presenting symptoms of RA, but who is found to possess a predisposition for developing RA, can be treated prophylactically or can make lifestyle changes to minimize his or her exposure to environmental risk factors in order to prevent the development of RA. A person seeking the present test for this purpose is likely to be one with a known family history of RA, but the present test method of the present invention are equally applicable to healthy individuals without any known family history of RA.

The following examples are given by way of illustration of the present invention and should not be construed to limit the scope of present invention.

Example 1

The RA patients were recruited through Army Hospital, Department of Rheumatology, New Delhi, India. The healthy controls were requited mainly through the Guru Teg Bahadur Hospital, Delhi, India. The Army Hospital rheumatologist thoroughly reviewed the medical records of the RA patients and the characterization of the disease was based on the revised criteria of the classification of the disease by American College of Rheumatology Classification criteria. The subject sample included 107 RA affected individuals and 121 normal healthy individual, all from Indian families. The Human Ethics Committee of the Army Hospital, Department of Rheumatology, N. Delhi, Delhi, India and that of the Institute of Genomics and Integrative Biology, Mall Road, Delhi-110007, India, approved the present study.

Example 2

ELISA Assay for the Detection of Autoantibodies to MBL

The presence of anti-MBL autoantibodies was tested for in 107 RA patients and 121 healthy controls. The ELISA tests were conducted with respect to anti-MBL antibodies, using BSA in parallel as the negative control. All the measurements were made in triplicates. The serum of the patient with a higher value of the autoantibodies to MBL was included systematically in each of the assay plates as a positive control.

The method for the identification of the autoantibodies to MBL in the sera of RA patients and the healthy controls comprises of coating an ELISA plate (Nunc) at 37° C. for two hours with 100 µL/well of serum purified MBL (U.S. Biologicals) in a carbonate/bicarbonate-buffer (pH 9.6) at 0.5 µg/mL concentration. Following the steps of washing with Tris-buffered saline (TBS, pH 7.4) containing 0.05% Tween-20 (TBST), blocking of the unoccupied binding sites with 200 µL of 1% bovine serum albumin (BSA) in TBST to each well was performed and the plate was incubated at 37° C. for 1.5 hour.

Effecting the binding of autoantibodies to MBL present in the sera of RA patients and the controls with the coated serum purified MBL, one hundred µL/well of serum samples diluted to 1:100 in TBST containing 0.3% BSA and 10 mM EDTA were added to each well and plate was incubated at 37° C. for two hours.

Affecting the binding of HRP conjugated anti-human IgG $(Fab')_2$ fragment, the plate was washed with TBST and hundred µL/well peroxidase conjugated goat antihuman IgG, $(Fab')_2$ fragment (Sigma) diluted 1:5000 in TBST was added to each well and the plate was incubated at 37° C. for 1 hour.

After the washing step, 100 µL/well of tetramethylbenzidine (TMB) substrate in was used to develop the color. To stop the reaction 2N phosphoric acid was used and optical densities at 450 nm were measured.

The concentration of IgG reactive with MBL is being expressed in arbitrary units/mL of serum (AU/mL) considering the autoantibody level of the patient with higher value, which served as the positive control in each of the assay performed, as 1000 AU/mL. The standard curve was generated with each assay performed using the serial dilution of the said sample as shown in the FIG. 1. Accordingly, the amount of anti-MBL autoantibodies in the sera of the RA patients and the healthy controls was calculated.

Example 3

ELISA Assay for the Detection of Isotypes of Rheumatoid Factors (IgM RF and IgG RF)

The presence of isotypes of rheumatoid factors (IgM RF and IgG RF) was measured by ELISA tests in the RA patients and the healthy controls and the standard curve was generated with each assay performed using the serial dilution of the sample used for anti-MBL autoantibody assay.

ELISA assays were developed for the measurement of rheumatoid factors of IgM and IgG isotypes in the sera of RA patients and the healthy. Flat microtiter plates (Nunc) were coated with 100 µL/well of a 10 µg/mL solution of normal rabbit IgG (Fluka) in carbonate buffer for two hours at 37° C.

Affecting the binding of rabbit IgG, the unoccupied sites were blocked using 1% BSA for 1 hour at 37° C. Subsequently the plates were washed and incubated with serum samples diluted in TBST for two hours at 37° C. The sample dilution used were 1/10, 1/50, 1/100 and 1/1000 for both IgM and IgG RF but the final dilutions used were 1/100 because of low reactivity at the higher dilutions.

Affecting the binding of the IgM and IgG RF, the bound RF isotypes were detected with 1:10000 dilution of peroxidase conjugate anti-human IgM $(Fab')_2$ fragment (Sigma) with TBST and 1:5000 diluted peroxidase conjugate anti-human IgG $(Fab')_2$ fragment (Sigma) for an hour at 37° C.

After washing steps, 100 µL/well TMB substrate was added and the color development was stopped by the addition of 2N phosphoric acid. The optical density values were determined with the ELISA plate reader (Biorad) at 450 nm. BSA, a non-sense antigen was included as a negative control in each assay performed and the wells incubated with TBST instead of serum were used as the blanks.

The concentration of IgM and IgG RF is expressed in arbitrary units/mL of serum (AU/mL) considering the RF level of a patient with higher OD value as 1000 AU/mL. The standard curve was generated with each assay performed using the serial dilution of the said sample.

Example 4

Data Analysis

Mann-Whitney U-test was used to analyze significance of the difference found between the titers of the anti-MBL autoantibodies and the RF isotypes in the sera of the RA patients and the healthy controls of the present invention. The P-values less than or equal to 0.05 were considered significant.

An arbitrary cutoff value of two standard deviations (2 SD) above average of the healthy controls for all the assays was taken for all the further calculations.

For each assay performed the following indices were calculated: percent sensitivity and specificity under Bayesian model, positive predictive value (PPV), negative predictive value (NPV), positive likelihood ratio (PLR) and negative likelihood ratio (NLR) to examine the ratio of the probabilities of the test result in RA patients and the healthy controls. In addition, an ROC (receiver operating characteristic) analysis was carried out to compare test characteristics independently of predefined cutoff points across different tests and calculated the area under the curve (AUC).

The RA patients were categorized into severe and less severe RA patients on the basis of DAS-28 disease score calculator considering the number of tender joints involved; number of swollen joints; ESR and the physician's global assessment of disease activity score, disease duration, duration of morning stiffness, presence of extra-articular manifestations and the presence of bone deformities. Out of 107 RA patients, 75 were categorized as severe.

A comparison between the assays for anti-MBL autoantibodies, RF isotypes (IgM RF and IgG RF) and their association with disease severity, disease activity and joint damage was made. The assay with the best sensitivity and specificity to diagnose RA was determined. A ROC curve was generated to compare the area under the curves for all the antibody assays performed.

Example 5

Results

Figure 2:
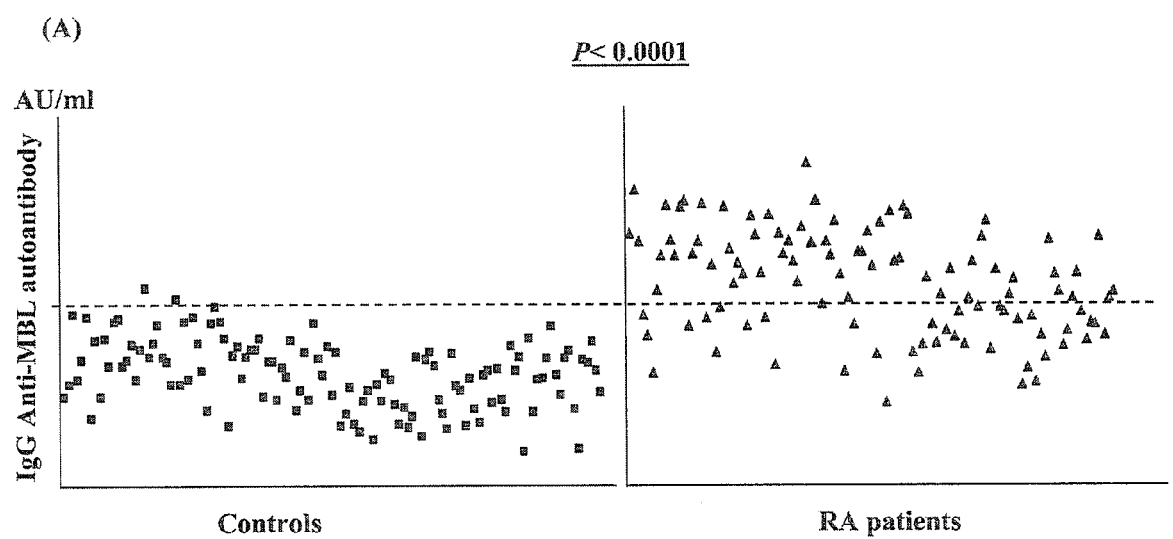
FIG. 2 represents a comparison of the anti-MBL autoantibodies in serum samples of controls and RA patients. P value was calculated by Mann-Whitney U-test and the AU/mL represents arbitrary units/mL of the serum samples.

In the present invention, the titer of anti-MBL autoantibodies in RA patients was found to be significantly higher (p≦0.0001 by Mann-Whitney U Test) than healthy controls. The mean±standard deviation (SD) was 427.487±129.398 AU/mL in the healthy controls and 747.722±192.417 AU/mL in the RA patients. The high OD value of a patient was designated as 1000 AU/mL and the titer of anti-MBL autoantibodies in the RA patients and the controls was thus computed. A cutoff level of 2 SD above the average of the anti-MBL autoantibodies in the control population, calculated as 686.28 AU/mL (as indicated by the dotted line in FIG. 2), was arbitrarily taken. The number of subjects having a titer of more than 2 SD above the average of the healthy controls was 65 out of 107 RA patients as compared to 2 out of 121 healthy controls. This difference was also found to be statistically significant (p=0.00001).

IgM RF was evaluated, in both the RA patients and the healthy controls, and was found to be statistically significant (p<0.001 by Mann-Whitney U test). The amount of IgM RF was 645.015±294.899 AU/mL (mean±SD) in the controls and 1359.231±682.618 AU/mL (mean±SD) in the RA patients. Also the difference in the level of IgG RF in the controls (mean±SD=840.849±146.077 AU/mL) and RA patients (mean±SD=1055.069±292.750 AU/mL) was statistically significant (p<0.001 by Mann-Whitney U test).

IgM and IgG RF isotypes were measured by ELISA and a cutoff level of 2 SD above average of the healthy controls was arbitrarily set. The number of cases having the titer of IgM RF more than 2 SD above average of the healthy controls (1234.814 AU/mL) was 55 out of 107 RA patients and 5 out of 121 healthy controls. However the number of cases with the amount of IgG RF more than 2 SD above average of the healthy controls (1133 AU/mL) was 31 out of 107 RA patients and 4 out of 121 healthy individuals. For both the RF isotypes this difference was statistically significant (p≦0.001).

In the present invention, for all the further comparisons of the diagnostic value of the anti-MBL autoantibodies and the RF isotypes a cutoff level of 2 SD above average of the control population was arbitrary set. Considering the 2 SD above average of the healthy controls for all the assays performed the predictive value, sensitivity and specificity of each assay was determined. The assay for anti-MBL autoantibodies was found to be more efficient in identifying the RA patients (60.75% sensitivity) and negating the healthy controls (98.35% specificity) in comparison to both of the RF isotypes. Examination of the likelihood ratios for various test results confirmed the difference between the tests (Table I).

Figure 3:
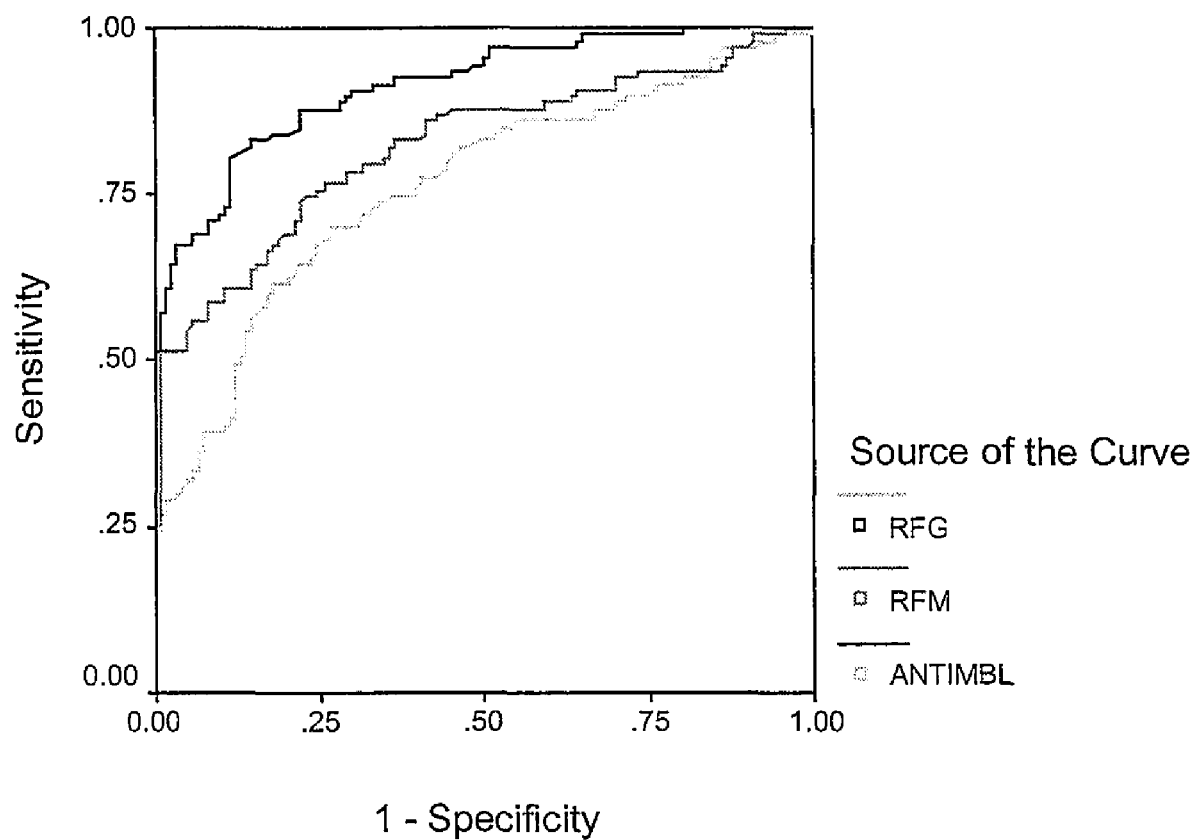
FIG. 3 represents the receiver operating characteristic curve of the anti-MBL autoantibodies and the RF isotypes (IgM RF and IgG RF).

For further comparisons of the diagnostic value for each assay, we undertook a ROC (receiver operating characteristic) analysis (FIG. 3) and calculated the area under the curve (AUC) with standard error (SE) and 95% confidence interval (CI). The ROC analysis displays the pairs of sensitivity and specificity for different cutoff points of anti-MBL autoantibodies, IgM RF and IgG RF concentrations. The AUC was best for anti-MBL autoantibodies (AUC=0.913, SE=0.019, 95% CI=0.876-0.949) while a further decrease was observed for IgM RF (AUC=0.822, SE=0.029, 95% CI=0.766-0.879) and IgG RF (AUC=0.761, SE=0.032, 95% CI=0.698-0.824). It could be seen that the anti-MBL autoantibodies provided the best combination of sensitivity and specificity for detecting rheumatoid arthritis.

In the present invention, an analysis of the benefits of combined use of all the three antibody assays was performed but found a decrease in the sensitivity in all the cases. However the combined assays were more specific for the detection of rheumatoid arthritis (Table I).

In 15.89% (17 out of 107) of all the RA patients investigated, all three antibodies were positive. However in 43 (40.18%) patients with clinically defined RA, the conventionally used RF isotypes (IgM RF and IgG RF) were all negative. In 27 (62.79%) of these 43 RA patients with negative RF isotypes, anti-MBL autoantibodies were still positive.

If only the IgM RF was used as a single RF test (most laboratories and Rheumatology departments of hospitals only measure IgM RF and not the other RF isotypes), as many as 52 (49.59%) patients with rheumatoid arthritis remained undetected. In IgM RF negative rheumatoid patients, anti-MBL autoantibodies were still positive in 34 (65.38%) of these 52 patients.

If both the RF isotypes (IgM and IgG RF) were negative, anti-MBL autoantibodies were still positive in 27 (25.23%) of all the 107 RA patients.

The RA patients were categorized into severe and less severe RA patients on the basis of DAS-28 disease score calculator considering the number of tender joints involved; number of swollen joints; ESR and the physician's global assessment of disease activity score, disease duration, duration of morning stiffness, presence of extra-articular manifestations, the presence of bone deformities and the acute phase response. Out of 107 RA patients, 75 were categorized as severe. Again considering the cutoff level of 2 SD above average of the healthy controls, 29.23% (19/65) of the less severe RA patients were anti-MBL autoantibody positive while a decreased number of less severe RA patients were

TABLE I

Sensitivity, specificity, positive predictive value (PPV), negative predictive value (NPV), positive likelihood ratio (PLR) and negative likelihood ratio (NLR) of serological markers in 107 RA patients.

| Serological marker | Sensitivity (%) | Specificity (%) | PPV (%) | NPV (%) | PLR | NLR |
|---|---|---|---|---|---|---|
| Anti-MBL autoantibody | 60.75 | 98.35 | 97.01 | 73.91 | 36.75 | 0.399 |
| IgM RF | 51.4 | 95.87 | 91.67 | 69.05 | 12.44 | 0.507 |
| IgG RF | 28.97 | 96.69 | 88.57 | 60.62 | 8.76 | 0.734 |
| Anti-MBL + IgM RF | 28.94 | 100 | 100 | 61.42 | ∝ | 0.710 |
| Anti-MBL + IgG RF | 22.43 | 98.35 | 92.31 | 58.91 | 13.57 | 0.785 |
| Anti-MBL + IgM RF + IgG RF | 15.89 | 100 | 100 | 57.35 | ∝ | 0.841 | found to be RF positive (25.45% for IgM RF and 12.90% for IgG RF). The diagnostic advantage of anti-MBL autoantibodies was even more convincing, where 11 of the 27 (40.74%) RA patients categorized as less severe RA patients were anti-MBL autoantibody positive but tested negative for both RF isotypes.

The RA patients were categorized according to the disease activity as per the DAS-28 disease score calculator. A DAS score of 5.1±1.61 (mean±SD) was calculated for all the 107 RA patients. A low disease activity, less than or equal to 3.49 DAS score (mean−SD) was reported in 16 RA patients (14.95%) while a moderate and high disease activity was observed in a higher number of RA patients. The prognostic accuracy of anti-MBL autoantibodies can be seen as the percentage of RA patients with positive anti-MBL autoantibodies was higher in all the cases as compared to both the RF isotypes and therefore showed a higher sensitivity than both the RF isotypes (Table II).

TABLE II

Data distribution depending on Anti-MBL auto antibodies,
IgG RF and IgM RF positivity in 107 RA patients.

| Clinical and paraclinical variables | Anti-MBL positive | Anti-MBL negative | IgM RF positive | IgM RF negative | IgG RF positive | IgG RF negative |
|---|---|---|---|---|---|---|
| Less severe RA (n = 32) | 16 | 16 | 13 | 19 | 4 | 28 |
| Severe RA (n = 75) | 49 | 26 | 42 | 33 | 27 | 48 |
| DAS <3.49 (n = 16) | 8 | 8 | 6 | 10 | 2 | 14 |
| DAS 3.49-5.1 (n = 22) | 11 | 11 | 8 | 14 | 3 | 19 |
| DAS 5.1-6.71 (n = 50) | 32 | 18 | 32 | 18 | 18 | 32 |
| DAS >6.71 (n = 19) | 12 | 7 | 9 | 10 | 8 | 11 |
| Tender joints (≧10) | 44 | 26 | 36 | 34 | 23 | 47 |
| Swollen joints (≧8) | 34 | 20 | 31 | 23 | 20 | 34 |
| Anti-MBL positive* | 65 | 42 | 31 | 34 | 24 | 41 |
| IgM RF positive* | 31 | 24 | 55 | 52 | 22 | 33 |
| IgG RF positive* | 24 | 6 | 22 | 8 | 31 | 76 |

*Anti-MBL auto antibodies level (AU/mL), IgG RF level (AU/mL), IgM RF level (AU/mL) ≧ Average ± 2 standard deviation. Seventy RA patients were found to have the number of Tender joints ≧10 (average of all RA patients). Fifty RA patients had swollen joints ≧8 (average of all RA patients), n = number of RA patients. Anti-MBL is the auto antibodies to MBL, IgM RF is the IgM isotype of rheumatoid factor, IgG RF is the IgG isotype of rheumatoid factor, DAS: Disease Activity Score.

50% (8/16) of the RA patients with a very low disease activity were anti-MBL autoantibody positive while only 37.5% (6/16) and 12.5% (2/16) were positive for IgM RF and IgG RF isotypes respectively. Similarly, a higher percentage of RA patients with a higher disease activity were anti-MBL autoantibody positive while the percentage tended to decrease when both the RF isotypes were considered. The proportion of rheumatoid arthritis patients with negative RF isotypes but positive anti-MBL autoantibodies were 14.81% (4/27) with low disease activity (DAS score≦3.49), 25.93% (7/27) with DAS score 3.49-5.1, 44.45% (12/27) with DAS score 5.1-6.71 and again 14.81% (4/27) with higher disease activity (DAS score≧6.71).

In the present invention, average±SD of the tender joints involved in all of the 107 RA patients were 10±6, 65.42% (70 out of 107) of the RA patients presented this severe joint destruction. 44 of these 70 patients (62.86%) were anti-MBL autoantibody positive while only 51.53% (36 out of 70) and 32.86% (23/70) of these RA patients was positive for IgM RF and IgG RF respectively. Also in the patients with higher number of tender joint, anti-MBL autoantibodies were more often present (62.86%) than in the patients with lower number of tender joints (56.76%). Again the percentage of RA patients with anti-MBL autoantibodies positive test and a lower number of tender joints involved were more (56.76%) as compared to IgM RF (48.65%) and IgG RF (24.32%) showing a higher sensitivity of anti-MBL autoantibodies to predict the presence of rheumatoid arthritis.

50.47 percent (54 out of 107) of our patient population had a high number of swollen joints (above average of all RA patients, 8±3=mean±SD). Out of these 54 RA patients, 62.96% were anti-MBL autoantibody positive while only 57.41% were IgM RF and 37.04% were IgG RF positive. A higher sensitivity of anti-MBL autoantibodies was observed to identify the RA patients with low number of swollen joints (below average of all the RA patients) as compared to both the RF isotypes. The number of RA patients that were anti-MBL autoantibody positive and with a low number of swollen joints was 30 out of 53 (56.60%) while it was 24/53 (45.28%) for IgM RF and 13/53 (25.53%) for IgG RF. Therefore of all the tests done anti-MBL autoantibodies showed the best method to detect the presence of joint damage.

We claim:

1. A method for the diagnosis of rheumatoid arthritis in a human subject suspected to be having rheumatoid arthritis, wherein the method comprises:
   comparing the levels of autoantibodies to mannose binding lectin (MBL) in the human subject suspected to be having rheumatoid arthritis to the level of autoantibodies to MBL in the blood of normal control individuals, as determined by ELISA;
   comparing the level of isotypes of rheumatoid factor antibodies IgM RF and IgG RF as determined using an ELISA test in the human subject suspected to be having rheumatoid arthritis to the level of rheumatoid factor antibodies IgM RF and IgG RF in the blood of normal control individuals; and
   wherein the possibility of rheumatoid arthritis in the human subject is indicated when:
   the level of autoantibodies to MBL in the human subject suspected to be having rheumatoid arthritis is greater than the level of autoantibodies to MBL in the blood of normal control individuals; and
   the level of isotypes of rheumatoid factor antibodies IgM RF and IgG RF in the human subject suspected to be having rheumatoid arthritis is greater than the level of rheumatoid factor antibodies IgM RF and IgG RF in the blood of normal control individuals.

2. The method as claimed in claim 1, wherein the possibility of rheumatoid arthritis in the human subject is indicated when the levels of MBL autoantibodies in the human subject is in the range from 753 to 1192 AU/mL.

3. The method as claimed in claim 1, wherein the possibility of rheumatoid arthritis in the human subject is indicated when the levels of MBL auto antibodies in the human subject is greater than 752 AU/mL.

4. The method as claimed in claim 1, wherein the presence of a level of autoantibodies to MBL (P value<0.0001) that is greater than the level of autoantibodies to MBL in the blood of normal control individuals, is associated with high disease rheumatoid arthritis (RA) activity and joint damage in the RA patient as compared to healthy individuals with out any symptoms of RA.

* * * * *